(12) United States Patent
Cosgrove et al.

(10) Patent No.: US 9,101,642 B2
(45) Date of Patent: Aug. 11, 2015

(54) TICAGRELOR CO-CRYSTAL

(75) Inventors: Stephen David Cosgrove, Cheshire (GB); David Thomas Jonaitis, West Lafayette, IN (US); Jonathan Charles Derrick Sutch, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 57 days.

(21) Appl. No.: 14/123,223

(22) PCT Filed: May 31, 2012

(86) PCT No.: PCT/GB2012/051222
§ 371 (c)(1),
(2), (4) Date: Jan. 29, 2014

(87) PCT Pub. No.: WO2012/164286
PCT Pub. Date: Dec. 6, 2012

(65) Prior Publication Data
US 2014/0148403 A1     May 29, 2014

Related U.S. Application Data

(60) Provisional application No. 61/491,949, filed on Jun. 1, 2011.

(51) Int. Cl.
| | |
|---|---|
| A01N 43/04 | (2006.01) |
| A61K 31/70 | (2006.01) |
| A61K 31/7064 | (2006.01) |
| A61K 31/706 | (2006.01) |
| C07H 19/16 | (2006.01) |
| A61K 31/7076 | (2006.01) |
| A61K 31/7042 | (2006.01) |
| A61K 31/7052 | (2006.01) |
| C07H 19/167 | (2006.01) |
| A61K 31/519 | (2006.01) |
| C07D 487/04 | (2006.01) |
| A61K 31/616 | (2006.01) |

(52) U.S. Cl.
CPC ........... *A61K 31/7064* (2013.01); *A61K 31/519* (2013.01); *A61K 31/616* (2013.01); *A61K 31/706* (2013.01); *A61K 31/7042* (2013.01); *A61K 31/7052* (2013.01); *A61K 31/7076* (2013.01); *C07D 487/04* (2013.01); *C07H 19/16* (2013.01); *C07H 19/167* (2013.01)

(58) Field of Classification Search
None
See application file for complete search history.

(56) References Cited

FOREIGN PATENT DOCUMENTS

| | | |
|---|---|---|
| WO | 0192262 | 12/2001 |
| WO | 02096428 | 12/2002 |
| WO | 2011067571 | 6/2011 |

OTHER PUBLICATIONS

Cheney et al., "Coformer selection in pharmaceutical cocrystal development: a case study of a meloxicam aspirin cocrystal that exhibits enhanced solubility and pharmacokinetics," Journal of Pharmaceutical Sciences (2010) 100 (6):2172-2181.
Shan et al., "The role of cocrystals in pharmaceutical science," Drug Discovery Today (2008) 13(9-10):440-446.

*Primary Examiner* — Patrick Lewis
(74) *Attorney, Agent, or Firm* — Pepper Hamilton LLP

(57) ABSTRACT

The present invention relates to a novel co-crystal of the compound of formula (I):

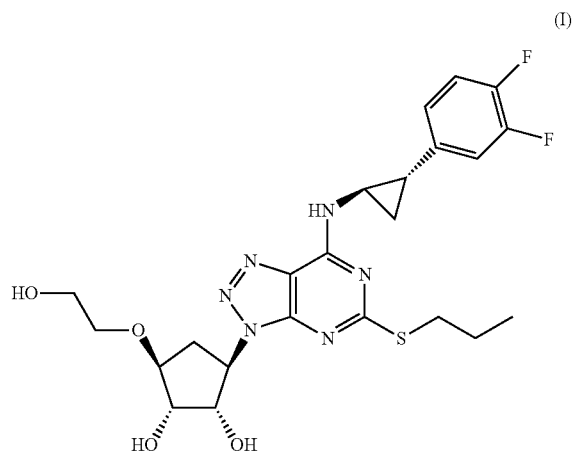

wherein the co-former molecule is acetyl salicylic acid, to processes for the preparation of the co-crystal, to pharmaceutical compositions containing the co-crystal, to the use of such a co-crystal in the manufacture of a medicament for use in the prevention of arterial thrombotic complications in patients with coronary artery, cerebrovascular or peripheral vascular disease and to methods of treating such diseases in the human or animal body by administering a therapeutically effective amount of a such a co-crystal.

17 Claims, 11 Drawing Sheets

Figure 1: XRPD of Compound A: acetyl salicylic acid co-crystal
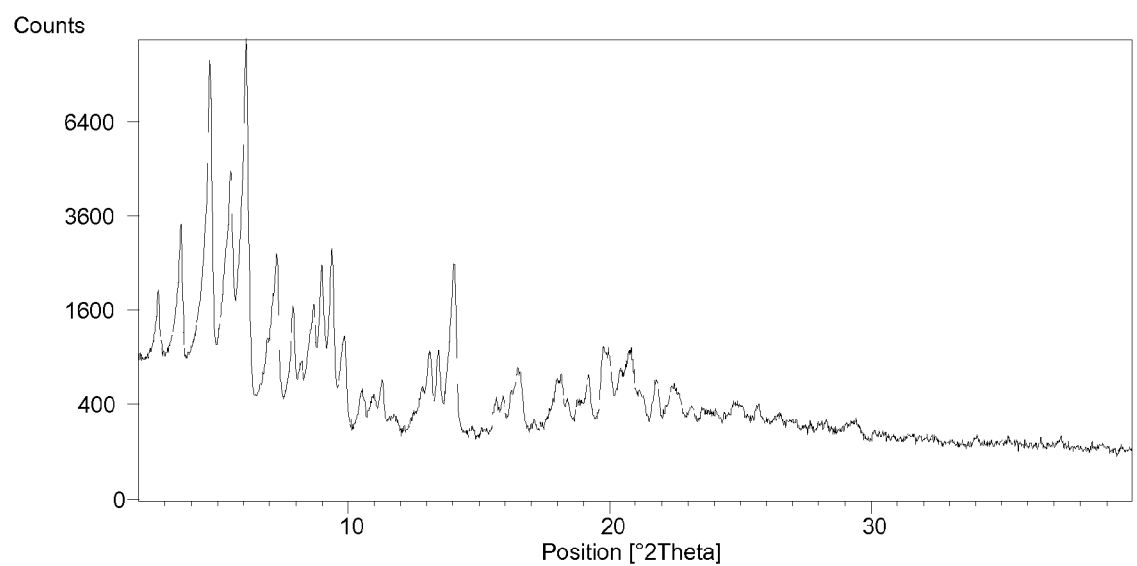

Figure 2 : Differential Scanning Calorimetry of Compound A: acetyl salicylic acid co-crystal, Compound A Form II and Acetyl salicylic acid (aspirin)
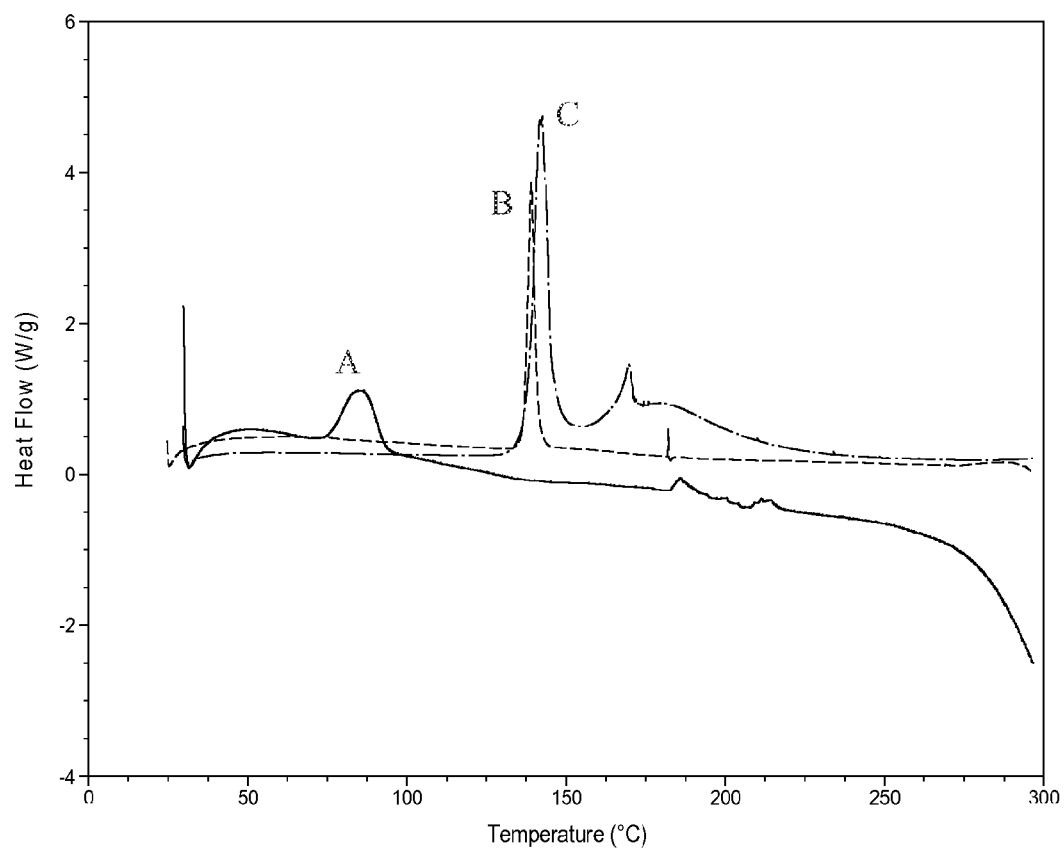
Trace A = Compound A: acetyl salicylic acid co-crystal
Trace B = Compound A Form II
Trace C = Acetyl salicylic acid (aspirin)

Figure 3: Thermogravimetric analysis of Compound A: acetyl salicylic acid co-crystal
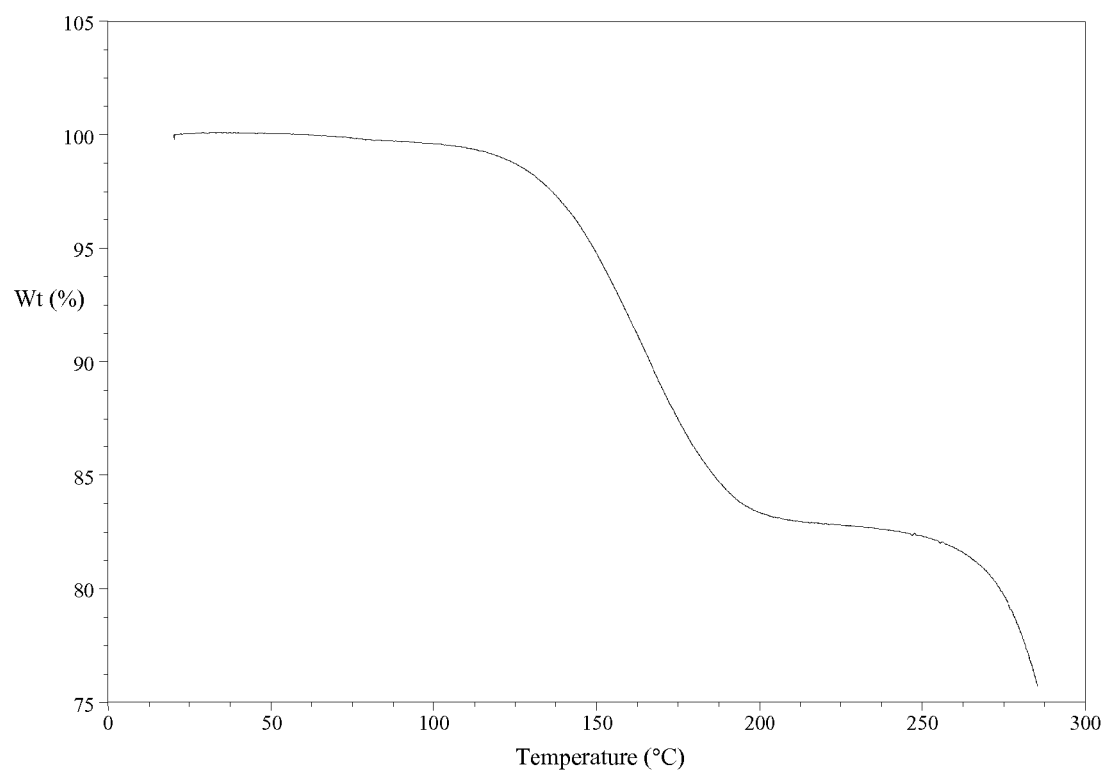

Figure 4: FTIR of Acetyl salicylic acid, Compound A Form II & Form III and Compound A: acetyl salicylic acid co-crystal
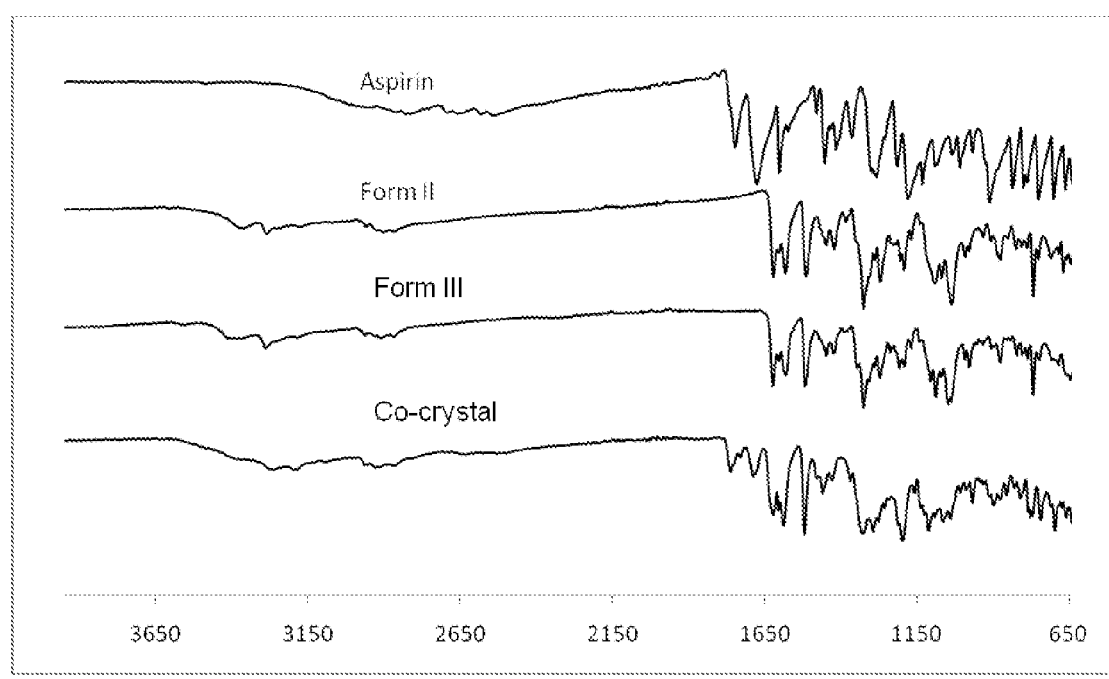

Figure 5: FTIR of Compound A: acetyl salicylic acid co-crystal
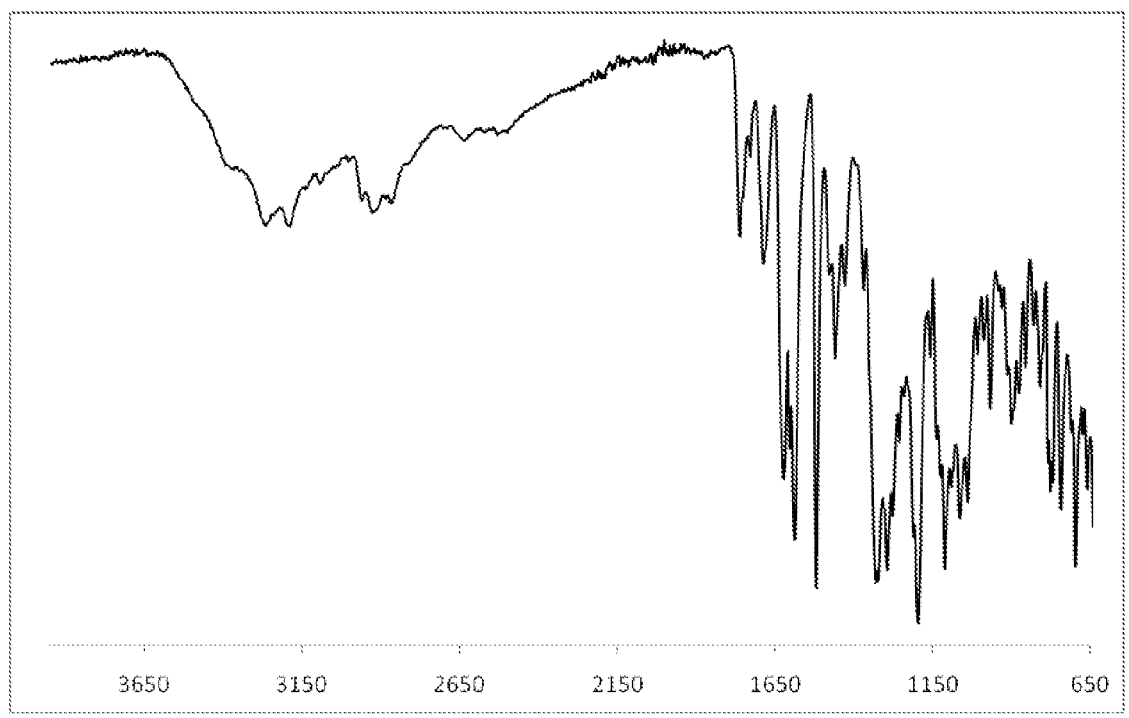

Figure 6: Solid state $^{13}$C NMR of Compound A: acetyl salicylic acid co-crystal
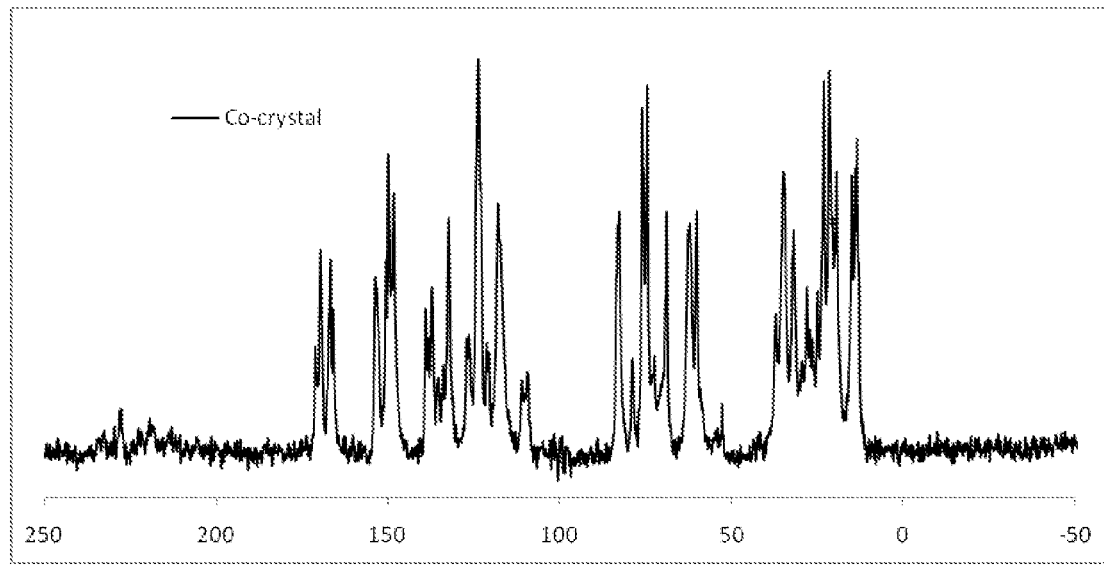
Figure 7: Solid state $^{13}$C NMR of Acetyl salicylic acid (aspirin)
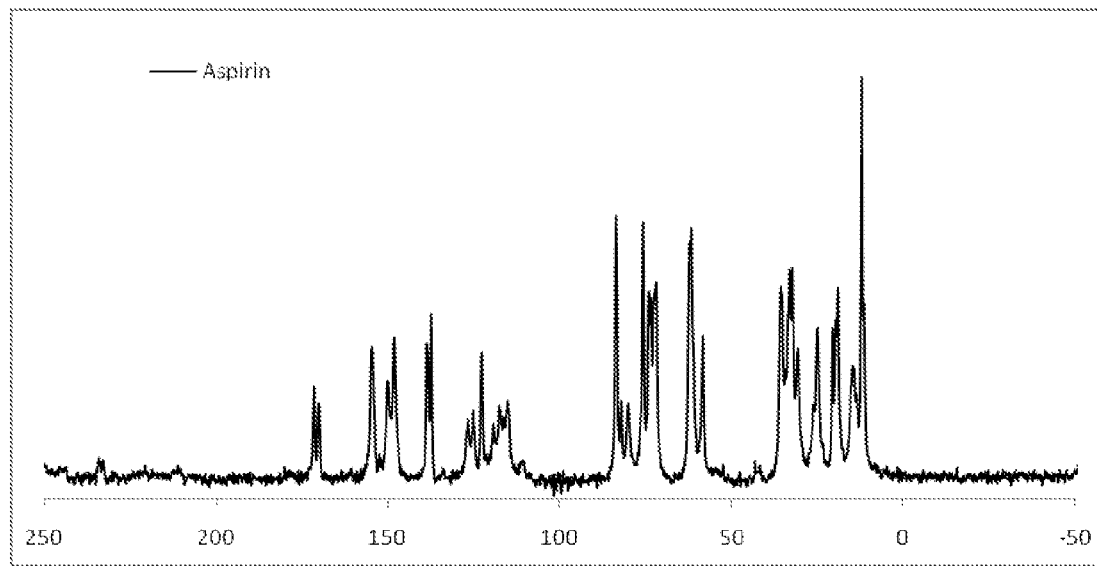

Figure 8: Solid state $^{13}$C NMR of Compound A Form I
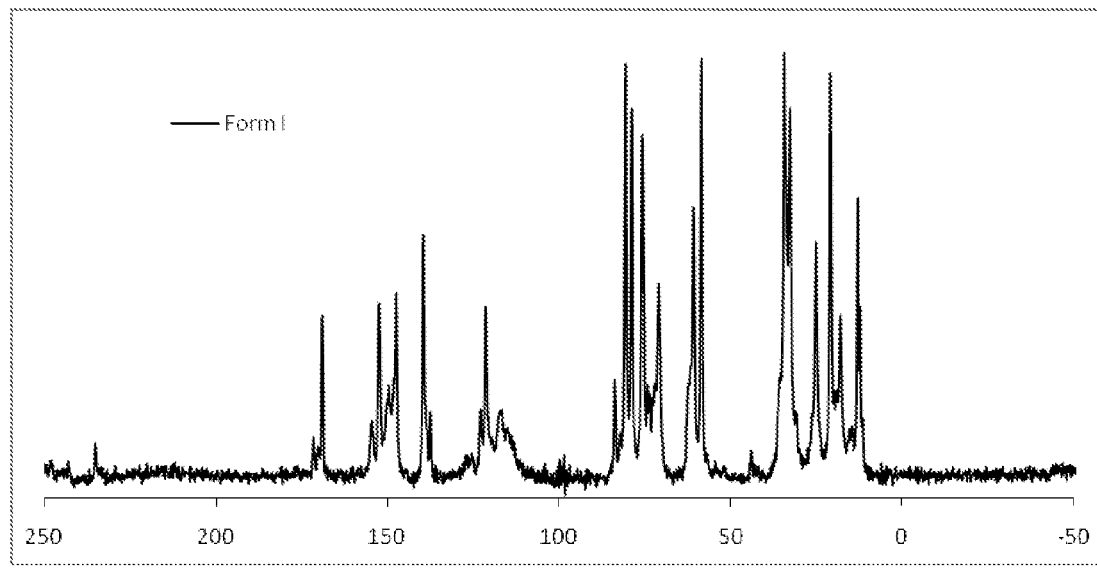
Figure 9: Solid state $^{13}$C NMR of Compound A Form II
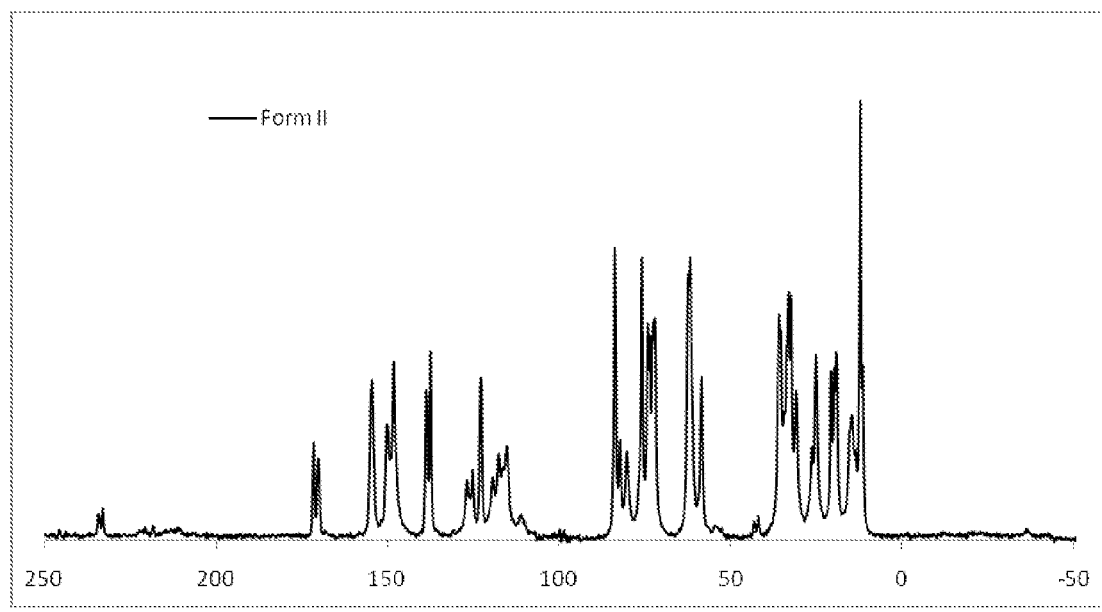

Figure 10: Solid state $^{13}$C NMR of Compound A Form III
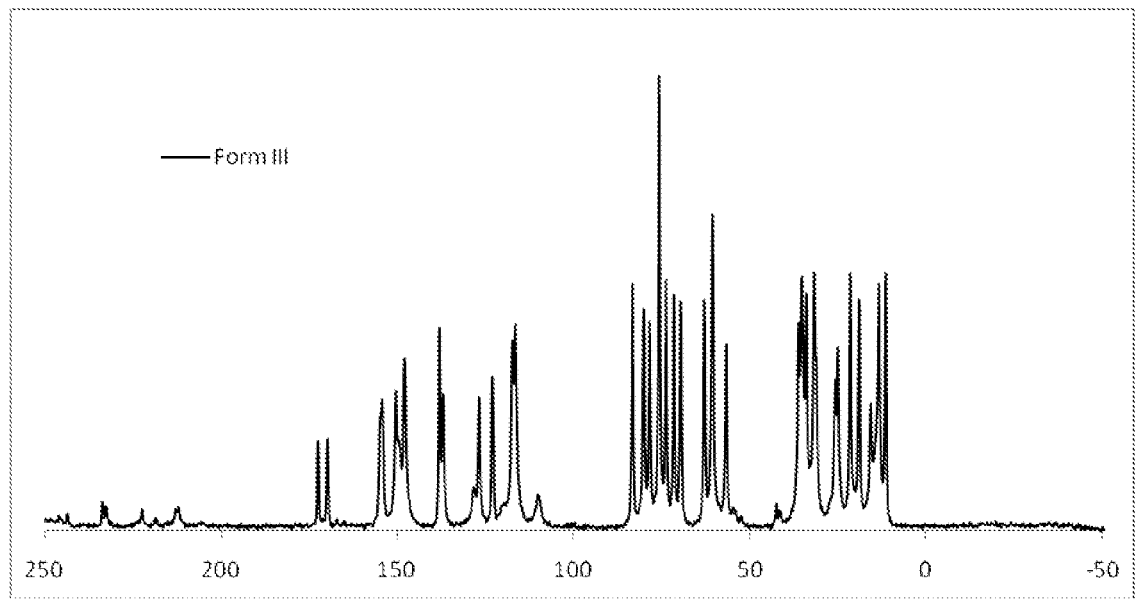

Figure 11: Liquid state $^1$H NMR of Compound A: acetyl salicylic acid co-crystal
A = relative integration of Acetyl salicylic acid (aspirin)
B = relative integration of Compound A
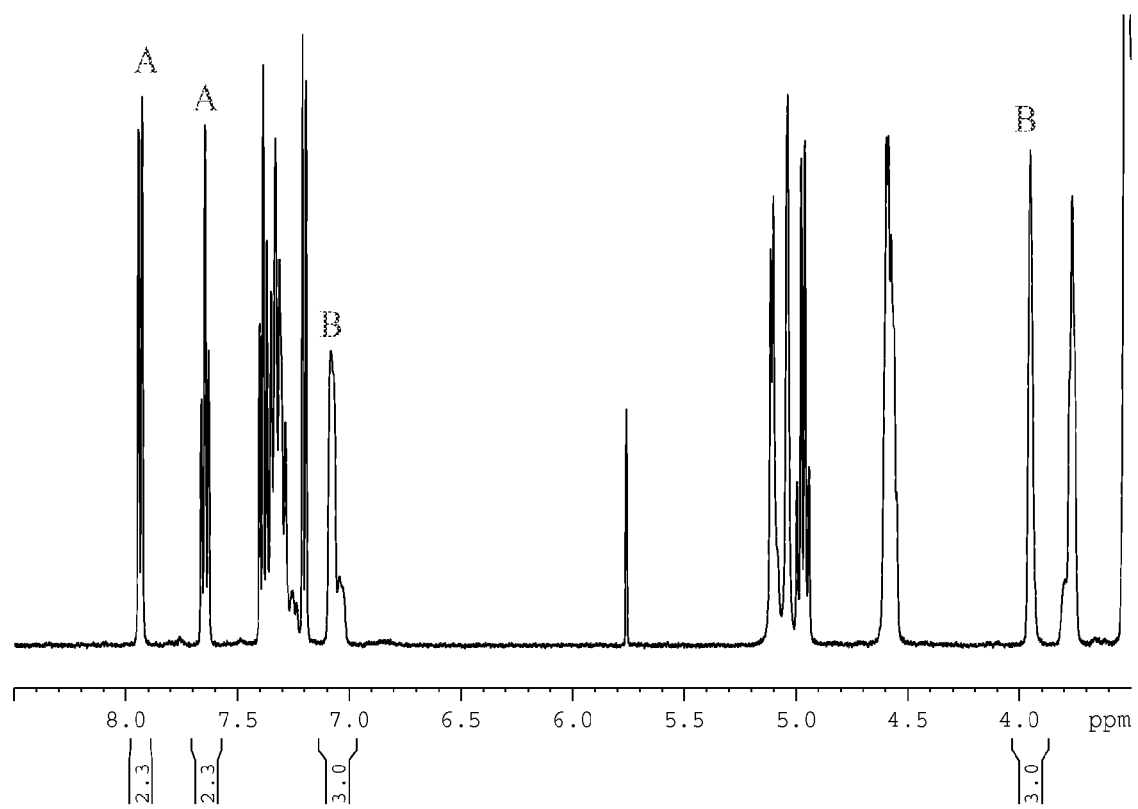

Figure 12: Dissolution profile of Compound A Form II and
Compound A: acetyl salicylic acid co-crystal in blank Fassif media over 240 minutes
(mean data of n=2)
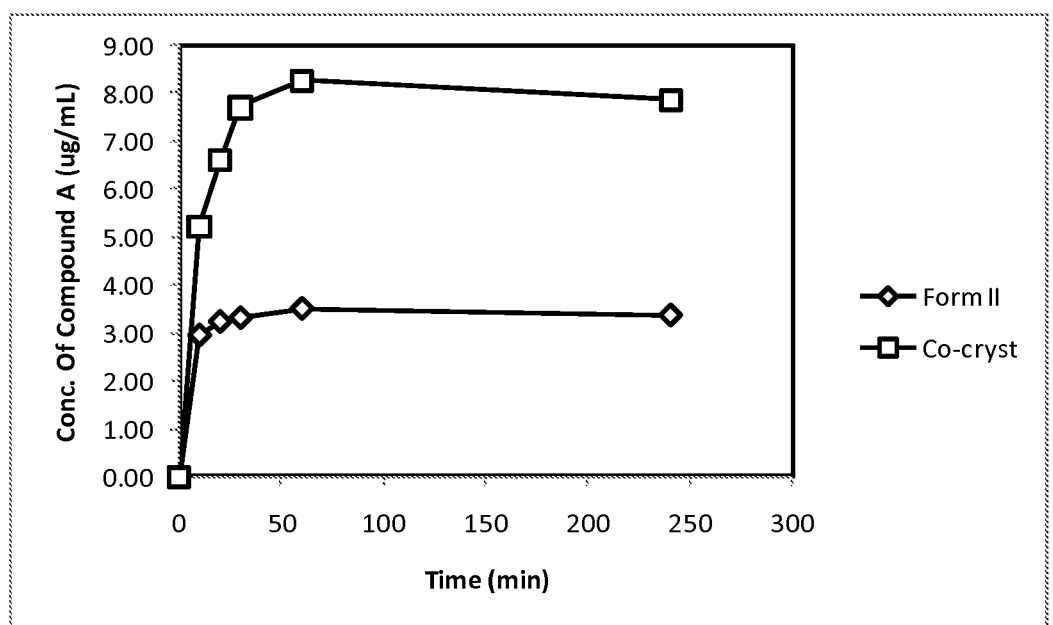

Figure 13: Dissolution profile of Compound A Form II and
Compound A: acetyl salicylic acid co-crystal in SGF media over 240 minutes
(mean data of n=2)
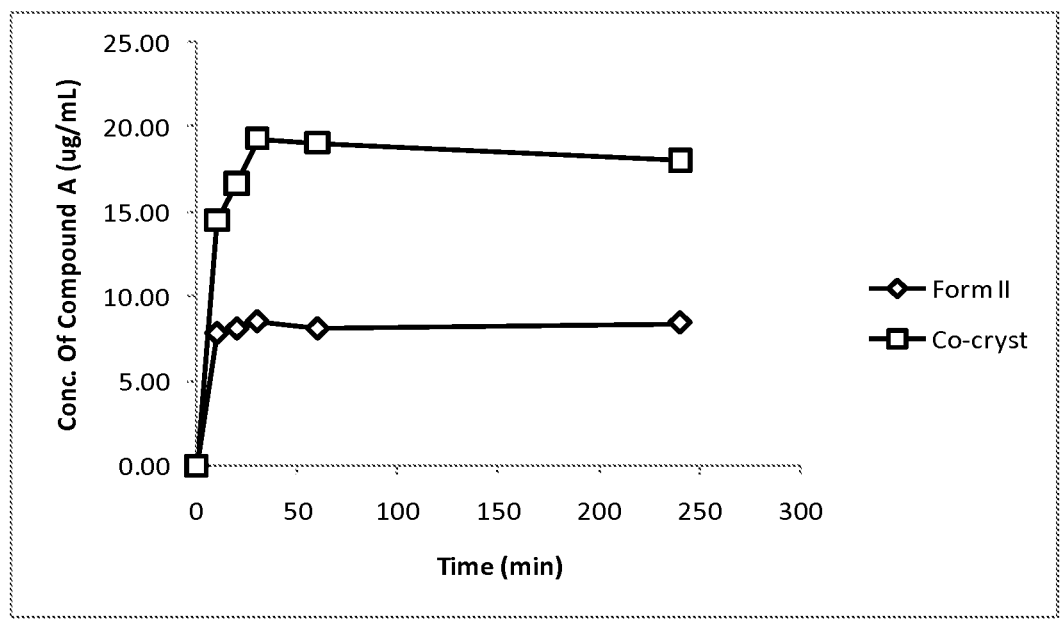

TICAGRELOR CO-CRYSTAL

The present invention relates to a novel co-crystal and more particularly to a novel co-crystal form of the compound of formula (I):

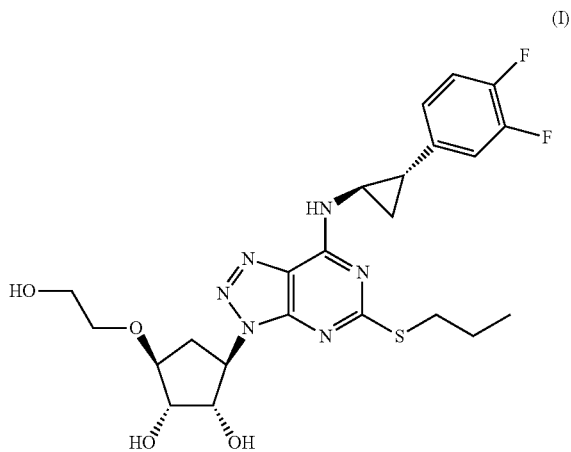 [SMILES: CCCSc1nc(N[C@@H]2C[C@H]2c2ccc(F)c(F)c2)c2nnn([C@@H]3C[C@H](OCCO)[C@@H](O)[C@H]3O)c2n1]

The compound of formula (I) is conventionally named: {1S-[1α,2α, 3β(1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol and is also known as ticagrelor, hereinafter named Compound A for convenience.

More specifically the invention relates to a co-crystal of Compound A, to processes for the preparation, to pharmaceutical compositions containing the co-crystal of Compound A, to the use of the co-crystal of Compound A in the manufacture of a medicament for use in the prevention of arterial thrombotic complications in patients with coronary artery, cerebrovascular or peripheral vascular disease and to methods of treating such diseases in the human or animal body by administering a therapeutically effective amount of a co-crystal of Compound A.

Platelet adhesion and aggregation are initiating events in arterial thrombosis. Although the process of platelet adhesion to the sub-endothelial surface may have an important role to play in the repair of damaged vessel walls, the platelet aggregation that this initiates can precipitate acute thrombotic occlusion of vital vascular beds, leading to events with high morbidity such as myocardial infarction and unstable angina. The success of interventions used to prevent or alleviate these conditions, such as thrombolysis and angioplasty are also compromised by platelet-mediated occlusion or re-occlusion.

It has been found that adenosine 5'-diphosphate (ADP) acts as a key mediator of thrombosis. ADP-induced platelet aggregation is mediated by the $P_{2T}$ receptor subtype located on the platelet membrane. The $P_{2T}$ receptor (also known as $P2Y_{ADP}$ or $P2T_{AC}$ or $P2Y_{12}$) is primarily involved in mediating platelet aggregation/activation and is a G-protein coupled receptor. The pharmacological characteristics of this receptor have been described, for example, in the references by Humphries et al., Br. J. Pharmacology (1994), 113, 1057-1063, and Fagura et al., Br. J. Pharmacology (1998) 124, 157-164. It has been shown that antagonists at this receptor offer significant improvements over other anti-thrombotic agents (see J. Med. Chem. (1999) 42, 213).

PCT International Patent Application WO 99/05143 discloses generically a series of triazolo[4,5-d]pyrimidine compounds having activity as $P_{2T}$ ($P2Y_{ADP}$ or $P2T_{AC}$) antagonists. Compound A is embraced by the generic scope of PCT International Patent Application WO 99/05143. Compound A exhibits high potency as a $P_{2T}$ ($P2Y_{ADP}$ or $P2T_{AC}$) antagonist and has a surprisingly high metabolic stability and bioavailability. Compound A is specifically exemplified in International Patent Application WO 00/34283 and may exist in a number of different substantially crystalline forms referred to hereafter as Polymorph I, Polymorph II, Polymorph III and Polymorph IV (or respectively, Form I, Form II, Form III and Form IV) as disclosed in PCT International Patent Application WO 01/92262.

Alternative forms of compounds in the form of a co-crystal can be useful for facilitating manufacturing and processing, for example of tablet forms and may also have potential for modulating properties such as solubility, dissolution, absorption, bioavailability and/or hygroscopicity over the free form.

The use of aspirin (acetyl salicylic acid) as a treatment for patients with, or at risk of a range of cardiovascular diseases, is recognised as a worldwide standard of care. Dual platelet inhibition therapy with a $P2Y_{12}$-inhibitor and acetyl salicylic acid is recognised as a worldwide standard of care in patients with acute coronary syndrome.

It has now been found that Compound A forms a co-crystal with a specific co-former molecule.

Accordingly, the present invention provides a co-crystal of the compound {1S-[1α, 2α,3β(1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol of formula (I) and a co-former molecule

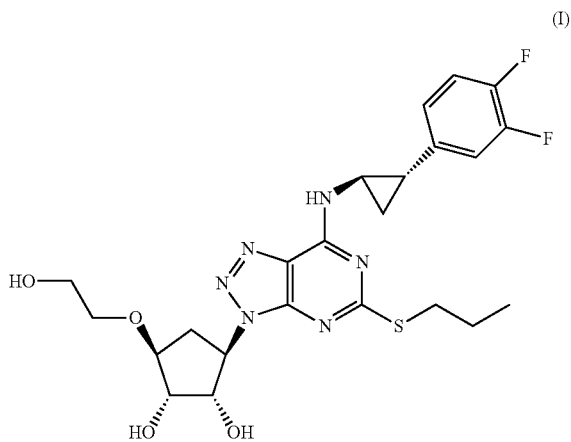 [SMILES: CCCSc1nc(N[C@@H]2C[C@H]2c2ccc(F)c(F)c2)c2nnn([C@@H]3C[C@H](OCCO)[C@@H](O)[C@H]3O)c2n1]

wherein the co-former molecule is acetyl salicylic acid.

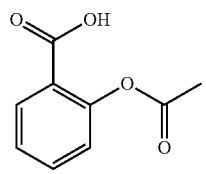

Acetyl salicyclic acid

Acetyl salicylic acid is also known as aspirin, and the terms are used interchangeably herein.

For the avoidance of doubt, the term co-crystal (or cocrystal) refers to a multicomponent system in which there exists a host API (active pharmaceutical ingredient) molecule or molecules and a guest (or co-former) molecule or molecules. In a co-crystal, both the API molecule and the guest (or co-former) molecule exist as a solid at room temperature when alone in their pure form (in order to distinguish the co-crystal from solvates or hydrates). Salts, in which significant or complete proton exchange occurs between the API molecule and the guest molecule, are excluded from this particular definition. In a co-crystal, the API and co-former molecules interact by hydrogen bonding and possibly other non-covalent interactions. It may be noted that a co-crystal may itself form solvates, including hydrates.

The present invention provides a co-crystal of Compound A with the co-former molecule acetyl salicylic acid and so provides a co-crystal in which both the host molecule and co-former molecule are API's (active pharmaceutical ingredients).

The invention also covers the co-crystal in any polymorphic or solvated (e.g. hydrated) form.

According to the present invention there is provided Compound A:acetyl salicylic acid co-crystal wherein said co-crystal is characterized by an X-ray powder diffraction pattern with specific peaks at about 2-theta (or d-spacing) as shown in Table 1.

TABLE 1

Primary reflections distinguishing Compound A: acetyl salicylic acid co-crystal from Compound A or pure aspirin solid forms

| Angle (°2 Theta) Measured at 1.5405 Å | d-spacing (Å) |
|---|---|
| 2.73, 3.60, 7.28, 8.68, 8.98, 9.87 | 32.3, 24.5, 12.1, 10.2, 9.8, 9.0 |

According to another aspect of the present invention there is provided Compound A:acetyl salicylic acid co-crystal wherein said co-crystal is characterized by an X-ray powder diffraction pattern with specific peaks (in addition to those in Table 1) at about 2-theta (or d-spacing) as shown in Table 2.

TABLE 2

Secondary reflections distinguishing Compound A: acetyl salicylic acid co-crystal from Compound A or pure aspirin solid forms

| Angle (°2 Theta) Measured at 1.5405 Å | d-spacing (Å) |
|---|---|
| 4.74, 6.12, 9.4, 11.31 | 18.6, 14.4, 9.4, 7.8 |

In Tables 1 and 2, d-spacing values below 5 Å are quoted to 2 decimal places (margin of error typically +/−0.05 Å), values above 5 Å may be rounded to one decimal place (margin of error typically +/−0.5 Å) and wherein 2-theta values are +/−0.2°.

In a further aspect of the invention, Compound A:acetyl salicylic acid co-crystal is characterized by an XRPD pattern substantially as shown in FIG. 1.

Compound A:acetyl salicylic acid co-crystal has an improved solubility profile compared to free form Compound A Form II (see WO 01/92262), see Example 5 herein. The properties of Compound A:acetyl salicylic acid co-crystal may allow alternative formulation options for Compound A.

In a specific embodiment of the invention, there is provided Compound A:acetyl salicylic acid co-crystal with a stoichiometry of Compound A:acetyl salicylic acid of approximately 3:2 (see Examples herein). The invention also covers the co-crystal in other stoichiometries of Compound A:acetyl salicylic acid.

In preparing Compound A:acetyl salicylic acid co-crystal as defined herein, a measured range of Compound A:acetyl salicylic acid molar ratios may be observed, reflecting a mixture of Compound A:acetyl salicylic acid co-crystal and a molar excess of Compound A and/or acetyl salicylic acid not incorporated in the co-crystal.

Mixtures comprising Compound A:acetyl salicylic acid co-crystal as defined herein with free Compound A and/or acetyl salicylic acid are within the scope of this invention; for example, mixtures comprising between 50 wt. % and 90 wt. % of Compound A:acetyl salicylic acid and the remainder comprising acetyl salicylic acid in free form and/or Compound A in free form. The remainder acetyl salicylic acid and/or Compound A in free form may each be in amorphous or crystalline form.

Mixtures comprising Compound A:acetyl salicylic acid co-crystal are covered by the invention and include, for example, greater than about 60% co-crystal, such as greater than about 80%, particularly greater than about 90%, more particularly greater than about 95% co-crystal, wherein the % co-crystal refers to the % by weight of the total sample mass of co-crystal.

In a further specific embodiment of the invention, Compound A:acetyl salicylic acid co-crystal, is in a mixture substantially free from other forms of Compound A and/or substantially free from excess acetyl salicylic acid and/or Compound A in free form; for example, a mixture comprising less than 10 wt. %, 5 wt. %, 3 wt. % or, more particularly, less than 1 wt. % of excess acetyl salicylic acid and/or Compound A in free form.

Thus, in one aspect, the present invention relates to a solid comprising a mixture of: (a) Compound A:acetyl salicylic acid co-crystal as defined herein and (b) acetyl salicylic acid.

Said solid may comprise, for instance, (a) 80-90 wt. % of Compound A:acetyl salicylic acid co-crystal as defined herein, and (b) 10-20 wt. % of acetyl salicylic acid.

In a further aspect, the present invention relates to a solid comprising a mixture of: (a) Compound A:acetyl salicylic acid co-crystal as defined herein and (b) amorphous Compound A and/or Polymorph I and/or Polymorph II and/or Polymorph III and/or Polymorph IV of Compound A.

In a further aspect, the present invention relates to a mixture of: (a) Compound A:acetyl salicylic acid co-crystal as defined herein and (b) amorphous Compound A and/or Polymorph I and/or Polymorph II and/or Polymorph III and/or Polymorph IV of Compound A which comprises a (wt. %) mixture of 80%-90% co-crystal with 10%-20% amorphous and/or Polymorph I and/or Polymorph II and/or Polymorph III and/or Polymorph IV of Compound A.

In a further aspect of the invention, there is provided Compound A:acetyl salicylic acid co-crystal obtainable by any of the processes or Examples mentioned herein.

In a further aspect of the invention, there are provided processes for the preparation of Compound A:acetyl salicylic acid co-crystal. For example, high saturation mixing of Compound A Form II and acetyl salicylic acid in a suitable solvent (e.g. dichloromethane)—see Examples herein.

Preparation of Compound A:acetyl salicylic acid co-crystal may be facilitated by use of the thermodynamically stable form of Compound A, i.e. Compound A Form III (see WO 01/92262), such that the solubility behaviour of Compound A does not vary as a result of phase changes between polymorphs of Compound A.

Compound A:acetyl salicylic acid co-crystal as defined herein is believed to liberate (in-vivo) Compound A, which acts as a $P_{2T}$ ($P2Y_{ADP}$ or $P2T_{AC}$) receptor antagonist, and acetyl salicylic acid. Accordingly, Compound A:acetyl salicylic acid co-crystal may facilitate simultaneous dosing of both Compound A and acetyl salicylic acid in patients to be administered both agents.

Compound A:acetyl salicylic acid co-crystal as defined herein is useful in therapy, including combination therapy with simultaneous, sequential or separate administration of at least one other pharmacologically active agent. In particular, Compound A:acetyl salicylic acid co-crystal as defined herein is indicated for use in the treatment or prophylaxis of arterial thrombotic complications in patients with coronary artery, cerebrovascular or peripheral vascular disease. Arterial thrombotic complications may include unstable angina, primary arterial thrombotic complications of atherosclerosis such as thrombotic or embolic stroke, transient ischaemic attacks, peripheral vascular disease, myocardial infarction with or without thrombolysis, arterial complications due to interventions in atherosclerotic disease such as angioplasty, including coronary angioplasty (PTCA), endarterectomy, stent placement, coronary and other vascular graft surgery, thrombotic complications of surgical or mechanical damage such as tissue salvage following accidental or surgical trauma, reconstructive surgery including skin and muscle flaps, conditions with a diffuse thrombotic/platelet consumption component such as disseminated intravascular coagulation, thrombotic thrombocytopaenic purpura, haemolytic uraemic syndrome, thrombotic complications of septicaemia, adult respiratory distress syndrome, anti-phospholipid syndrome, heparin-induced thrombocytopaenia and pre-eclampsia/eclampsia, or venous thrombosis such as deep vein thrombosis, venoocclusive disease, haematological conditions such as myeloproliferative disease, including thrombocythaemia, sickle cell disease; or in the prevention of mechanically-induced platelet activation in vivo, such as cardio-pulmonary bypass and extracorporeal membrane oxygenation (prevention of microthromboembolism), mechanically-induced platelet activation in vitro, such as use in the preservation of blood products, e.g. platelet concentrates, or shunt occlusion such as in renal dialysis and plasmapheresis, thrombosis secondary to vascular damage/inflammation such as vasculitis, arteritis, glomerulonephritis, inflammatory bowel disease and organ graft rejection, conditions such as migraine, Raynaud's phenomenon, conditions in which platelets can contribute to the underlying inflammatory disease process in the vascular wall such as atheromatous plaque formation/progression, stenosis/restenosis and in other inflammatory conditions such as asthma, in which platelets and platelet-derived factors are implicated in the immunological disease process.

According to a further aspect of the present invention there is provided Compound A:acetyl salicylic acid co-crystal as defined herein for use in a method of treatment of the human or animal body by therapy.

According to an additional feature of the present invention there is provided Compound A:acetyl salicylic acid co-crystal as defined herein for use as a medicament. Particularly, Compound A:acetyl salicylic acid co-crystal as defined herein is used as a medicament to antagonise the $P_{2T}$ ($P2Y_{ADP}$ or $P2T_{AC}$) receptor in a warm-blooded animal such as a human being. More particularly, Compound A:acetyl salicylic acid co-crystal as defined herein is used as a medicament for treating or preventing arterial thrombotic complications in patients with coronary artery, cerebrovascular or peripheral vascular disease in a warm-blooded animal such as a human being.

According to the invention there is further provided the use of Compound A:acetyl salicylic acid co-crystal as defined herein in the manufacture of a medicament for use as an antagonist of the $P_{2T}$ ($P2Y_{ADP}$ or $P2T_{AC}$) receptor. In particular there is further provided the use of Compound A:acetyl salicylic acid co-crystal as defined herein in the manufacture of a medicament for use in the treatment or prevention of arterial thrombotic complications in patients with coronary artery, cerebrovascular or peripheral vascular disease.

The invention also provides a method of treatment or prevention of arterial thrombotic complications in patients with coronary artery, cerebrovascular or peripheral vascular disease, which comprises administering to a person suffering from or susceptible to such a disorder a therapeutically effective amount of Compound A:acetyl salicylic acid co-crystal as defined herein.

Compound A:acetyl salicylic acid co-crystal as defined herein may be administered topically, e.g. to the lung and/or the airways, in the form of solutions, suspensions, HFA aerosols and dry powder formulations; or systemically, e.g. by oral administration in the form of tablets, pills, capsules, syrups, powders or granules, or by parenteral administration in the form of sterile parenteral solutions or suspensions, by subcutaneous administration, or by rectal administration in the form of suppositories or transdermally.

Compound A:acetyl salicylic acid co-crystal as defined herein may be administered on its own or as a pharmaceutical composition comprising Compound A:acetyl salicylic acid co-crystal as defined herein in combination with a pharmaceutically acceptable diluent, adjuvant and/or carrier. Therefore there is provided as a further feature of the invention a pharmaceutical composition comprising Compound A:acetyl salicylic acid co-crystal as defined herein in association with a pharmaceutically acceptable diluent, adjuvant and/or carrier. Particularly preferred are compositions not containing material capable of causing an adverse reaction, such as an adverse allergic reaction.

Dry powder formulations and pressurised HFA aerosols of Compound A:acetyl salicylic acid co-crystal as defined herein may be administered by oral or nasal inhalation. For inhalation Compound A:acetyl salicylic acid co-crystal as defined herein is desirably finely divided. Compound A:acetyl salicylic acid co-crystal as defined herein may also be administered by means of a dry powder inhaler. The inhaler may be a single or a multi dose inhaler, and may be a breath actuated dry powder inhaler.

One possibility is to mix the finely divided Compound A:acetyl salicylic acid co-crystal as defined herein with a carrier substance, e.g. a mono-, di- or polysaccharide, a sugar alcohol or another polyol. Suitable carriers include sugars and starch. Alternatively the finely divided Compound A:acetyl salicylic acid co-crystal as defined herein may be coated by another substance. The powder mixture may also be dispensed into hard gelatine capsules, each containing the desired dose of Compound A:acetyl salicylic acid co-crystal as defined herein.

Another possibility is to process the finely divided powder into spheres which break up during the inhalation procedure. This spheronized powder may be filled into the drug reservoir of a multidose inhaler, e.g. that known as the Turbuhaler® in which a dosing unit meters the desired dose which is then inhaled by the patient. With this system Compound A:acetyl salicylic acid co-crystal as defined herein, with or without, a carrier substance is delivered to the patient.

The pharmaceutical composition comprising Compound A:acetyl salicylic acid co-crystal as defined herein may conveniently be tablets, pills, capsules, syrups, powders or granules for oral administration; sterile parenteral or subcutaneous solutions, suspensions for parenteral administration or suppositories for rectal administration.

Microdissolution data (see Example 5) in aqueous buffers at physiologically relevant pHs (e.g. blank FASSIF—without micelle forming components) demonstrate that Compound A:acetyl salicylic acid co-crystal has improved solubility in non-micellar systems compared to free Compound A Form II. This indicates that the co-crystal is likely to have improved solubility in the lower regions of the GI tract (where micelle forming components are not significantly present compared to the higher GI tract), which may result in improved absorption of Compound A from this region when dosed as a co-crystal rather than Compound A Form II in the free form. This would increase the feasibility of achieving a modified release formulation for delivery of Compound A over an extended period, for example 12-24 hours, that could provide suitable plasma exposures following once-daily dosing. Furthermore, the use of Compound A:acetyl salicylic acid co-crystal in a suitable formulation would permit the simultaneous dosing of both Compound A and acetyl salicylic acid active pharmaceutical ingredients.

For oral administration Compound A:acetyl salicylic acid co-crystal as defined herein may be admixed with an adjuvant or a carrier, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated, the tablet cores may be coated with a concentrated sugar solution which may contain e.g. gum arabic, gelatine, talcum, titanium dioxide, and the like. Alternatively, the tablet may be coated with a suitable polymer dissolved either in a readily volatile organic solvent or an aqueous solvent.

Alternatively, Compound A:acetyl salicylic acid co-crystal may be formulated with excipients which modify the rate of drug release, to provide means for sustained delivery of the co-crystal to the lower GI tract in order to prolong the absorption phase. Such a formulation could be administered alone or combined with an immediate release component as required to provide suitable plasma concentrations.

A controlled release formulation may comprise a polymer that controls the active ingredient to be released in a suitable amount. The polymer may be any controlled release polymer that is conventionally used in the art for preparing controlled release dosage forms. Examples of such polymers include, but not limited to, water insoluble polymers, water soluble polymers, enteric polymers, and the like, and mixtures thereof.

Suitable water insoluble polymers include, but not limited to, cellulose derivatives, such as ethylcellulose; acrylic polymers, such as polyacrylamide, polyacrylic dextrin, polyalkylcyanoacrylates, polymethylmethacrylates and methacrylic resins; polyvinyl acetate; polyvinyl chloride; polyethylene; and the like; and mixtures thereof.

If present, a water insoluble polymer preferably comprises about 2% to about 30% by weight, more preferably about 4% to about 25%, and most preferably from about 6% to about 20% by weight of the pharmaceutical composition.

Suitable water soluble polymers include, but are not limited to, hydroxypropylcellulose, hydroxypropylmethylcellulose ("HPMC"), carboxymethylcellulose, xanthan gum, polyvinylpyrrolidone ("PVP") and the like, and mixtures thereof, e.g., hydroxypropyl methyl cellulose and xanthan gum. In particular, the water soluble polymer is hydroxypropylcellulose or hydroxypropylmethylcellulose. More specifically, the polymer is hydroxypropylmethycellulose. If present, the water soluble polymer is present in an amount preferably ranging from about 0.01% to about 8% by weight, and more preferably from about 0.1 to about 4% by weight and most preferably from about 0.25 to about 2% by weight of the pharmaceutical composition.

Suitable enteric polymers include, but not limited to, cellulose acetate phthalate, hydroxypropylmethylcellulose acetate succinate, carboxymethylcellulose, styrene acrylic copolymers, methacrylic copolymers, maleic anhydride copolymers, shellac, and the like, and mixtures thereof. If present, it is preferably present in about 2% to about 30% by weight of the pharmaceutical composition, more preferably from about 4% to about 25% by weight and most preferably from about 6% to about 20% by weight of the pharmaceutical composition.

A suitable release-controlling polymer may comprise one or more of the above described polymers. For instance, the water soluble polymer may be used alone. In one embodiment, ethylcellulose is used alone or in combination with another water soluble polymer, enteric polymer or insoluble polymer. The water insoluble polymer may be used in combination with another water insoluble polymer, enteric polymer or water soluble polymer. Finally, the enteric polymer may be used in combination with another enteric polymer, water soluble polymer or water insoluble polymer. The water soluble polymer may also be used in combination with a water insoluble polymer. In another embodiment, ethylcellulose is used in combination with hydroxypropylcellulose or hydroxypropylmethylcellulose. In addition, the enteric polymer may also be used alone. Furthermore, it is possible to use two polyacrylates. A still further embodiment uses the combination of acrylic acid and a methacrylate polymer. The controlled release polymer coatings can be an organic solvent or aqueous latex based dispersion.

The amount of release-controlling-film-forming polymer should be sufficient to effectively control the drug to be released in a desired amount at a desired rate.

Examples of gelling agents that may be present include such substances as hydroxypropylcellulose, hydroxymethylcellulose, hydroxyethylcellulose, hydroxypropyl ethylcellulose, methylcellulose, ethylcellulose, carboxyethylcellulose, carboxymethyl hydroxyethylcellulose, carbomer, sodium carboxymethylcellulose, polyvinylpyrrolidone, and the like, or mixtures thereof.

For the preparation of soft gelatine capsules, Compound A:acetyl salicylic acid co-crystal as defined herein may be admixed with e.g. a vegetable oil or polyethylene glycol. Hard gelatine capsules may contain granules of the compound using either the above mentioned excipients for tablets, e.g. lactose, saccharose, sorbitol, mannitol, starches, cellulose derivatives or gelatine. Also liquid or semisolid formulations of the drug may be filled into hard gelatine capsules.

Alternatively, Compound A:acetyl salicylic acid co-crystal may be formulated in a drug delivery system intended for prolonged gastrointestinal retention. Various mechanisms are possible, such as mucoadhesion, flotation, sedimentation, swelling and unfolding, or by co-administration of pharmacological agents which delay gastric emptying. In mucoadhesion, a suitable polymer is incorporated causing the drug delivery system to adhere to the gastrointestinal mucus layer while the drug is released. Suitable polymers include polycarbophils, carbomers, alginates, chitosan, gums, lectins, cellulose and cellulose derivatives or mixtures thereof. In flotation, the delivery system incorporates matrices containing chambers of entrapped gas or generates these following administration by use of a swellable matrix with an effervescent couple, such as sodium bicarbonate; hence the dosage unit has a bulk density lower than gastric fluid and remains buoyant in the stomach. In case of sedimentation or densification as a mechanism for gastroretention, the dosage form has high bulk density compared to the density of gastric contents. Such systems, usually multiparticulates, are retained in the rugae or folds of the stomach near the pyloric region and tend to withstand the peristaltic movements of the stomach wall, significantly prolonging intestinal transit time. Controlled-release drug delivery systems for gastric retention have been extensively reviewed (see for example: Journal of Controlled Release, 63 (2000) 235-259, "Floating drug delivery systems: an approach to oral controlled drug delivery via gastric retention" Singh, B. N., Kim, K. H.; J Control. Release, 2003; 90 (2): 143-62, "Expandable gastroretentive dosage forms". Klausner E. A., Lavy E, Friedman M, Hoffman A.; AAPS Pharm. Sci. Tech. 2005; 6 (3) Article 47 "Floating drug delivery systems—a review" Arora, S., Ali, J., Ahuja, A., Khar, R. K., Baboota, S.; Exp. Opin. Drug. Deliv. 2006; 3 (2): 217-33, "Gastroretentive drug delivery systems". Streubel A, Siepmann J, Bodmeier R.).

Liquid preparations for oral application may be in the form of syrups or suspensions, for example solutions containing Compound A:acetyl salicylic acid co-crystal as defined herein, the balance being sugar and a mixture of ethanol, water, glycerol and propylene glycol. Optionally such liquid preparations may contain colouring agents, flavouring agents, saccharine and carboxymethylcellulose as a thickening agent or other excipients known to those skilled in the art.

Compound A:acetyl salicylic acid co-crystal as defined herein is believed to liberate Compound A, which acts as a $P_{2T}$ ($P2Y_{ADP}$ or $P2T_{AC}$) receptor antagonist as disclosed in International Patent Application No. WO 00/34283, and acetyl salicylic acid is which acts as an antiplatelet agent. The pharmacological properties of Compound A and Compound A:acetyl salicylic acid co-crystal described herein may be assessed, for example, using one or more of the procedures set out in International Patent Application No. WO 00/34283. For example, the preparation for the assay of the $P_{2T}$ ($P2Y_{ADP}$ or P2Tc) receptor agonist/antagonist activity in washed human platelets is set out in International Patent Application No. WO 00/34283 wherein antagonist potency is estimated as a % inhibition of the control ADP response to obtain an $IC_{50}$. In WO 00/34283, compounds exemplified therein are reported to have $pIC_{50}$ values of more than 5.0.

EXAMPLES

The invention is illustrated herein by means of the following non-limiting Examples, data and Figures in which, unless otherwise stated:—
(i) yields are given for illustration only and are not necessarily the maximum attainable;
(ii) where product is used for seeding it can be obtained by prior known or disclosed processes.

The co-former acetyl salicylic acid (also referred to interchangeably as aspirin herein) is a readily available material and was used in the following experiments with Compound A (which can be prepared as described in the PCT applications mentioned herein—the relevant contents of which are incorporated herein by reference).

Standard analysis techniques that can be used include XRPD, FTIR to help characterise H-bonding, solid-state NMR, solution state NMR, DSC and TGA. More details are provided in the Examples and in the following paragraphs on X-ray powder diffraction.

It is known in the art that an X-ray powder diffraction pattern may be obtained which has one or more measurement errors depending on measurement conditions (such as equipment, sample preparation or machine used). In particular, it is generally known that intensities in an X-ray powder diffraction pattern may fluctuate depending on measurement conditions and sample preparation. For example, persons skilled in the art of X-ray powder diffraction will realize that the relative intensities of peaks may vary according to the orientation of the sample under test and on the type and setting of the instrument used so that the intensities in the XRPD traces included herein are illustrative and not intended to be used for absolute comparison.

The skilled person will also realise that the position of reflections can be affected by the precise height at which the sample sits in the diffractometer and the zero calibration of the diffractometer. The surface planarity of the sample may also have a small effect.

Hence a person skilled in the art will appreciate that the diffraction pattern data presented herein is not to be construed as absolute (for further information see Jenkins, R & Snyder, R. L. 'Introduction to X-Ray Powder Diffractometry' John Wiley & Sons, 1996).

It is also stated above that, in general, a measurement error of a diffraction angle in an X-ray powder diffractogram is about 2–theta=0.5° or less (or, more suitably, about 2–theta=0.2° or less) and such degree of a measurement error should be taken into account when considering the X-ray powder diffraction patterns, and when interpreting the peak positions referred to in the text above and in the Tables herein. D-spacing values below 5 Å are quoted to 2 decimal places (margin of error typically +/−0.05 Å), values above 5 Å may be rounded to one decimal place (margin of error typically +/−0.5 Å) and wherein 2-theta values are +/−0.2°.

BRIEF DESCRIPTION OF FIGURES

FIG. 1 shows the XRPD of Compound A:acetyl salicylic acid co-crystal (see Example 4).

FIG. 2 shows the DSC curve of Compound A:acetyl salicylic acid co-crystal (see Example 4).

FIG. 3 shows the TGA curve of Compound A:acetyl salicylic acid co-crystal (see Example 4).

FIG. 4 shows the IR spectra of acetyl salicylic acid, Compound A Form II, and Compound A:acetyl salicylic acid co-crystal, respectively (see Example 4).

FIG. 5 shows the IR spectra of Compound A:acetyl salicylic acid co-crystal (see Example 4).

FIG. 6 shows the solid state NMR of Compound A:acetyl salicylic acid co-crystal (see Example 4).

FIG. 7 shows the solid state NMR of acetyl salicylic acid (see Example 4).

FIG. 8 shows the solid state NMR of Compound A Form I (see Example 4).

FIG. 9 shows the solid state NMR of Compound A Form II (see Example 4).

FIG. 10 shows the solid state NMR of Compound A Form III (see Example 4).

FIG. 11 shows the liquid state NMR of Compound A:acetyl salicylic acid co-crystal (see Example 4).

FIG. 12 shows the dissolution profile of Compound A Form II and Compound A:acetyl salicylic acid co-crystal in blank Fassif media (see Example 5).

FIG. 13 shows the dissolution profile of Compound A Form II and Compound A:acetyl salicylic acid co-crystal in SGF media (see Example 5).

EXAMPLE 1

Preparation of Compound A:Acetyl Salicylic Acid Co-Crystal by Slurry

Acetyl salicylic acid (aspirin) was added to 600 μL of dichloromethane with sonication until a suspension was obtained and solid persisted. Compound A Form II (see WO 01/92262) was added to the resulting mixture until both aspirin and Compound A were present in the solid phase.

The presence of both materials in the solid phase was determined by visual inspection; the aspirin had a needle habit and Compound A consisted of small particles.

The resulting slurry was stirred at ambient temperature for approximately 2 hours and then centrifuged. The liquid was removed by decantation and treated with a solid mixture of 50 mg (0.096 mmol) of Compound A Form II and 18 mg (0.010 mmol) of aspirin. The resulting slurry was stirred at ambient temperature for about 3 days, adding additional dichloromethane as necessary, and then vacuum filtered.

The resulting solid (67 mg), a free-flowing white powder, was analyzed by XRPD.

The XRPD comprised peaks which could not be accounted for by the known forms of Compound A or of aspirin. These peaks were subsequently confirmed to be those denoted as Compound A:acetyl salicylic acid co-crystal (see Example 4 and FIG. 1).

EXAMPLE 2

Preparation of Compound A:Acetyl Salicylic Acid Co-Crystal by Slurry

Compound A Form III was produced by slurrying Form II (see WO 01/92262) in dichloromethane with Form III seed material (prepared, for example, as described in WO 01/92262) for 2 days at room temperature.

Hexanes (0.75 mL) was added to a mixture of 3.3 mg (0.00631 mmol) of Compound A Form III (produced as described above) and 3.6 mg (0.0120 mmol) of aspirin. The resulting mixture was treated with 50-μL portions of dichloromethane, with sonication between additions, until all of the solid dissolved (1.4 mL was required). That solution was added to a mixture of 31.1 mg (0.0595 mmol) of Compound A Form III (produced as described above) and 10.7 mg (0.0594 mmol) of aspirin. The resulting slurry was stirred at ambient temperature for 11 days and centrifuged. The liquid was removed by decantation and the solid was dried in a stream of dry air to give 35.2 mg) of Compound A:acetyl salicylic acid co-crystal (78% yield based on a co-crystal stoichiometry of 3:2 Compound A:acetyl salicylic acid—see Example 3).

The resulting solid gave a diffractogram consistent with peaks listed in Example 4 (see FIG. 1).

EXAMPLE 3

Preparation of Compound A:Acetyl Salicylic Acid Co-Crystal by Cooling

Dichloromethane (1.5 mL) was added to a mixture of 31.0 mg (0.0593 mmol) of Compound A Form III (prepared as described in Example 2) and 10.7 mg (0.0594 mmol) of aspirin. Sonication of the mixture produced a slightly turbid solution, which was seeded with approximately 5 mg of co-crystal (prepared, as for example, in Example 2) and kept in a refrigerator overnight, during which time crystallization occurred. A white solid was recovered by vacuum filtration to give 20.8 mg of solid material (54% yield based on a co-crystal stoichiometry of 3:2 Compound A:acetyl salicylic acid—see below).

The resulting solid gave an XRP diffractogram consistent with peaks listed in Example 4 (see FIG. 1) for Compound A:acetyl salicylic acid co-crystal, with no evidence of Compound A or aspirin polymorphs in the XRPD diffractogram.

Integration of the $^1$H solution state NMR spectral peaks showed hydrogens consistent with aspirin in approximately a 2:3 ratio with respect to Compound A, indicative of co-crystal material with approximately a 3:2 Compound A:acetyl salicylic acid stoichiometry.

Differential Scanning calorimetry (DSC) gave a trace broadly consistent with that of Example 4 (see FIG. 2), with an endothermic event at ~80° C. and no defined melting events attributable to either aspirin or the four polymorphic forms of Compound A.

Thermogravimetric analysis (TGA) was consistent with that of Example 4 (see FIG. 3), and gave a mass loss of 1% w/w up to ~100° C., significantly lower than any % w/w loss expected for a DCM solvate. An additional loss of 15.4% w/w between 100 and 225° C. is attributable to volatilization/decomposition of the aspirin co-former (expected 18.7% w/w).

Analysis Details for Examples 1-3

XRPD analyses were performed on a Scintag X1 Advanced Diffraction System equipped with a Vortex Silicon Multi-Cathode detector. Data were collected using Cu Kα radiation (1.5418 Å). The X-Ray tube voltage and amperage were set to 45 kV and 40 mA, respectively. The slits used were a 1 mm divergence slit, a 2 mm tube scatter slit, a 0.5 mm detector scatter slit, and a 0.3 mm reference slit. Data were collected in continuous mode from 2 to 40°2θ using a 0.02 degree step and a 1 second collection time per step. Each sample was prepared for analysis by placing it in the 1-mm deep, round well of a stainless steel holder and leveling the surface with a glass slide.

DSC analyses were carried out using a TA Instruments 2920 instrument. Samples were prepared in crimped aluminum pans and kept under a flow of nitrogen during analysis. The heating rate was 10° C./minute.

Thermogravimetric analyses (TGA) were carried out using a TA Instruments 2050 instrument. Samples were kept under a flow of nitrogen during analysis. The heating rate was 10° C./minute.

Liquid state $^1$H NMR spectra were acquired on a Bruker DRX-500 spectrometer located at the Chemistry Department of Purdue University. Samples were prepared by dissolving material in chloroform-d3. The solutions were filtered and placed into individual 5-mm NMR tubes for subsequent spectral acquisition.

Temperature controlled (298K) $^1$H NMR spectrum were acquired on the DRX-500 utilized a 5-mm cryoprobe operating at an observing frequency of 499.89 MHz and a 30° to pulse width (10.8 μsec) with 32k data points, 64 co-averaged scans, 2.340 sec acquisition time, 7.0 kHz sweep width, and 2.0 sec delay time between pulses. Data processing (Fourier transform of the FID, phasing, baseline correction, integration, image generation) were carried out with the NMR data processing program NUTS Lite (Acorn NMR Inc.). Spectra were referenced to the 7.24 ppm peak of CHCl$_3$.

EXAMPLE 4

Further Preparation of Compound A:Acetyl Salicylic Acid Co-Crystal by Cooling Dichloromethane (DCM) (23 mL) was added to a mixture of 1.04 g (1.99 mmol) of Compound A Form III (see Example 2) and 360 mg (2.00 mmol) of aspirin. Sonication of the mixture produced a slightly turbid solution which was refrigerated for approximately 10 minutes and then seeded with about 25 mg of Compound A:acetyl salicylic acid co-crystal (prepared, for example, as described in Example 2). The sample was kept in a refrigerator for about 3 days, during which time crystallization occurred. A white solid was recovered by vacuum filtration and placed in a $P_2O_5$ dessicator for two hours under vacuum to give 851 mg of Compound A:acetyl salicylic acid co-crystal (67% yield based on a co-crystal stoichiometry of 3:2 Compound A:acetyl salicylic acid—see Example 3).

EXAMPLE 4

Analysis Details

X-ray Powder Diffraction (XRPD)

Data was collected using a Philips X-Pert MPD machine in θ-2θ configuration over the scan range 2° to 40° 2θ with 5995-second exposure per 0.0167° increment, with ⅓₂° incident beam. The X-rays were generated by a copper long-fine focus tube operated at 45 kV and 40 mA. The wavelengths of the copper X-rays were 1.5405 Å ($K\alpha_1$). The data was collected on zero background holders on which ~2 mg of the sample was placed. The holder was made from a single crystal of silicon, which had been cut along a non-diffracting plane and then polished on an optically flat finish. The X-rays incident upon this surface were negated by Bragg extinction.

XRPD of the sample gave rise to a diffraction pattern, with intense reflections due to the Compound A:acetyl salicylic acid co-crystal at 32.3, 24.5, 12.1, 10.2, 9.8 and 9.0 Å and more specifically 32.3, 24.5, 18.6, 14.4, 12.1, 10.2, 9.8, 9.4, 9.0 and 7.8 Å.

TABLE 1

Primary reflections distinguishing Compound A: acetyl salicylic acid co-crystal from Compound A or pure aspirin solid forms

| Angle (°2 Theta) Measured at 1.5405 Å | d-spacing (Å) |
|---|---|
| 2.73, 3.60, 7.28, 8.68, 8.98, 9.87 | 32.3, 24.5, 12.1, 10.2, 9.8, 9.0 |

TABLE 2

Secondary reflections distinguishing Compound A: acetyl salicylic acid co-crystal from Compound A or pure aspirin solid forms

| Angle (°2 Theta) Measured at 1.5405 Å | d-spacing (Å) |
|---|---|
| 4.74, 6.12, 9.4, 11.31 | 18.6, 14.4, 9.4, 7.8 |

FIG. 1 shows the XRPD pattern of Compound A:acetyl salicylic acid co-crystal.

Note that the diffractogram of this material shows no evidence of the presence of crystalline aspirin nor known crystalline forms of Compound A.

Thermal Gravimetric Analysis and Differential Scanning Calorimetry

Thermal data was collected using a TGA 2050 instrument. Samples were kept under a flow of nitrogen during analysis. The heating rate was 10° C./minute.

Thermogravimetric analysis (TGA) shows that there are two distinct regions in which mass loss is seen (see FIG. 3). The first at around 80° C. in which the mass is reduced by less than 1% consistent with presence of DCM, as observed in the solution state NMR. The second mass loss in which the mass is reduced by 17% is attributable to partial volatilisation of the aspirin co-former (expected 18.7% w/w).

In addition, differential scanning calorimetry (DSC) of Compound A:acetyl salicylic acid co-crystal (see FIG. 2) showed no thermal events within 40° C. of any of the melting points of the known crystalline forms of Compound A or of aspirin (the known crystalline forms of Compound A melt in the range of approximately 127-152° C. and crystalline aspirin melts at about 138° C.). The DSC is consistent with results obtained in Example 3. In FIG. 2, trace A shows Compound A:acetyl salicylic acid co-crystal, trace B shows Compound A Form II, and trace C shows acetyl salicylic acid.

Thermal analysis does not show the presence of any of the known crystalline forms of Compound A or of aspirin. TGA is indicative of anhydrate co-crystal material.

Infrared Spectroscopy

IR spectra (see FIGS. 4 and 5) were obtained on a Nicolet 6700 FT-IR system, with Golden gate ATR, CDFIR004. A resolution of 4 cm$^{-1}$ was used with 32 scans collected. A scan range of 4000-600 cm$^{-1}$ was used with a torque of 20 cNm.

Infra-red spectroscopy data indicates the presence of bands due to both Compound A and aspirin, but shifted. The shift in the positions of the peaks, particularly in the region of hydrogen bonding shows the form is not a simple physical mixture and is indicative of co-crystal formation. Peaks specific to the co-crystal include 3266 (a), 3190 (a), 1730, 1590 (a) 1521 (a) 1199 (a) 699 (asa) cm-1 and more specifically also include, 1461, 1430, 1322, 1114, 1066, 1080, 1061, 902, 812, 779, 745, 676, 627 cm-1 (where asa=acetylsalicylic acid peaks, a=Compound A peaks).

For reference, infra-red spectroscopy of Compound A Form II, exhibits distinguishing peaks at 3373, 3248, 3177, 2962, 2924 and 2907 cm$^{-1}$.

For reference, infra-red spectroscopy of Compound A Form III, exhibits distinguishing peaks at 3376, 2913, 2871, 1519, 1107, 1090 and 1049 cm$^{-1}$.

For reference, infra-red spectroscopy of aspirin, exhibits distinguishing peaks at 2282, 2654, 2583, 2542, 1749 1678, 1482, 1417, 1365, 1181, 1134 and 1011 cm$^{-1}$.

Solid State $^{13}$C NMR

Solid-state $^{13}$C NMR data (see FIGS. 6 to 10) was collected on Bruker Avance 500 MHz spectrometer. For $^{13}$C experiments a spinning speed of 12 kHz was used at the magic angle.

$^{13}$C Solid-state NMR of the co-crystal gave rise to peaks with chemical shifts that are specific to the co-crystal at 166.8, 166.0, 134.1, 132.5 and 23.3 ppm and more specifically 166.8, 153.8, 166.0, 153.8, 134.1, 132.5, 123.9, 74.7, 69.0 and 23.3 ppm.

Liquid State $^1$H NMR $^1$H NMR was collected using a Bruker Avance 500 MHz NMR spectrometer. Samples were prepared by dissolving in deuterated DMSO solvent.

Liquid state $^1$H NMR (see FIG. 11) was used to measure the relative signals of Compound A and aspirin and showed they were present in the ratio of 3:2.3 (Compound A:aspirin), consistent with analysis from Example 3 and indicating approximately a 3:2 co-crystal of Compound A:aspirin. In addition, a small amount of DCM is observable in the NMR at a level of 0.1% mols relative to Compound A). In FIG. 11, A shows the relative integration of acetyl salicylic acid, and B shows the relative integration of Compound A.

EXAMPLE 5

Dissolution Work

Micro-dissolution investigations were performed on 9 mg of a sample of Compound A:acetyl salicylic acid co-crystal (prepared as described in Example 4) or Compound A Form II in both 25 ml of (i) Fasted intestinal fluid (Fassif) without micelle forming components (termed blank Fassif) and (ii) of Simulated Gastric Fluid (SGF). The samples were magnetically stirred and aliquots were taken at appropriate time intervals, centrifuged and the supernatant analysed by HPLC and the concentration of Compound A measured as a function of time.

Simulated Gastric Fluid (SGF) media was prepared by adding 131.5 ml 1M HCl to 4 g NaCl and the resulting solution made up to 2 Liters with milli-Q water (de-ionised water).

Fasted intestinal fluid without micelle forming components (blank Fassif) media was prepared from 0.348 g NaOH pellets, 3.954 g $NaH_2PO_4.H_2O$ and 6.186 g NaCl in 1 L milli-Q water. The pH was then adjusted to pH 6.5 with 1N NaOH or 1N HCl.

Microdissolution studies demonstrated that Compound A:aspirin co-crystal (Compound A:acetyl salicylic acid co-crystal) showed an approximately 2 fold increase in solubility compared to Form II of Compound A in both Blank Fassif (see FIG. 12, Tables 3A and 3B) and SGF (see FIG. 13, Tables 4A and 4B) media.

TABLE 3A

Compound A Form II in blank Fassif, dissolution data (mean data of n = 2)

| Time (mins) | Concentration of Compound A (µg/ml) |
| --- | --- |
| 0 | 0.00 |
| 10 | 2.95 |
| 20 | 3.24 |
| 30 | 3.31 |
| 60 | 3.51 |
| 240 | 3.37 |

TABLE 3B

Compound A: aspirin co-crystal in blank Fassif, dissolution data (mean data of n = 2)

| Time (mins) | Concentration of Compound A (µg/ml) |
| --- | --- |
| 0 | 0.00 |
| 10 | 5.23 |
| 20 | 6.62 |
| 30 | 7.72 |
| 60 | 8.26 |
| 240 | 7.88 |

TABLE 4A

Compound A Form II in SGF, dissolution data (mean data of n = 2)

| Time (mins) | Concentration of Compound A (µg/ml) |
| --- | --- |
| 0 | 0.00 |
| 10 | 7.82 |
| 20 | 8.10 |
| 30 | 8.52 |
| 60 | 8.10 |
| 240 | 8.45 |

TABLE 4B

Compound A: aspirin co-crystal in SGF, dissolution data (mean data of n = 2)

| Time (mins) | Concentration of Compound A (µg/ml) |
| --- | --- |
| 0 | 0.00 |
| 10 | 14.48 |
| 20 | 16.69 |
| 30 | 19.32 |
| 60 | 19.07 |
| 240 | 18.04 |

The invention claimed is:

1. A co-crystal of the compound {1S-[1α,2α,3β(1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol of formula (I), named Compound A for convenience, and a co-former molecule

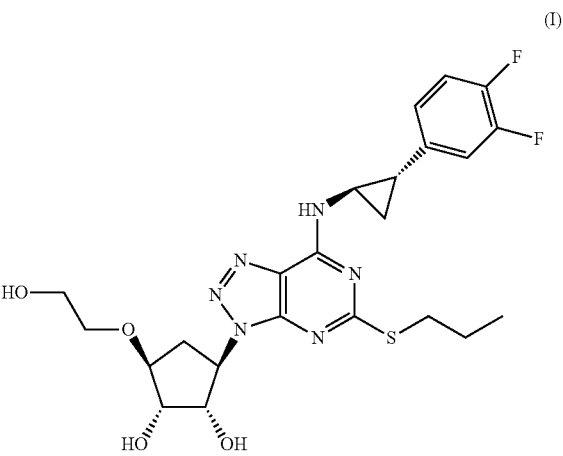 [SMILES: CCCSc1nc(N[C@@H]2C[C@H]2c2ccc(F)c(F)c2)c2nnn([C@@H]3C[C@H](OCCO)[C@@H](O)[C@H]3O)c2n1]

(I)

wherein the co-former molecule is acetyl salicylic acid.

2. A co-crystal of the compound of formula (I) and acetyl salicylic acid according to claim 1, characterised in that it has an X-ray powder diffraction pattern with peaks as shown in the following Table

| Angle (°2 Theta) Measured at 1.5405 Å | d-spacing (Å) |
| --- | --- |
| 2.73, 3.60, 7.28, 8.68, 8.98, 9.87 | 32.3, 24.5, 12.1, 10.2, 9.8, 9.0 | wherein 2-theta values are +/−0.2°.

3. A co-crystal of the compound of formula (I) and acetyl salicylic acid according to claim 2, characterised in that it has an X-ray powder diffraction pattern with peaks in addition to those in claim 2 as shown in the following Table

| Angle (°2 Theta) Measured at 1.5405 Å | d-spacing (Å) |
| --- | --- |
| 4.74, 6.12, 9.4, 11.31 | 18.6, 14.4, 9.4, 7.8 | wherein 2-theta values are +/−0.2°.

4. A co-crystal of the compound of formula (I) and acetyl salicylic acid according to claim 1, characterised in that it has a stoichiometry of approximately 3:2 Compound A:acetyl salicylic acid.

5. A method of preparing a co-crystal of the compound of formula (I) and acetyl salicylic acid as defined in claim 1, said method comprising mixing a suspension of the compound of formula (I) and acetyl salicyclic acid in a suitable solvent.

6. A method of preparing a co-crystal of the compound of formula (I) and acetyl salicylic acid as defined in claim 5, wherein the compound of formula (I) polymorph III is used.

7. A pharmaceutical composition comprising a co-crystal of the compound of formula (I) and acetyl salicylic acid, as defined in claim 1, and a pharmaceutically acceptable diluent or carrier.

8. A method of treating arterial thrombotic complications in patients with coronary artery, cerebrovascular or peripheral vascular disease by administering a therapeutically effective amount of a co-crystal of the compound of formula (I) and acetyl salicylic acid as defined in claim 1.

9. A co-crystal of the compound of formula (I) and acetyl salicylic acid according to claim 2, characterised in that it has a stoichiometry of approximately 3:2 Compound A:acetyl salicylic acid.

10. A co-crystal of the compound of formula (I) and acetyl salicylic acid according to claim 3, characterised in that it has a stoichiometry of approximately 3:2 Compound A:acetyl salicylic acid.

11. A method of preparing a co-crystal of the compound of formula (I) and acetyl salicylic acid as defined in claim 5, wherein said suitable solvent is dichloromethane.

12. A pharmaceutical composition comprising a co-crystal of the compound of formula (I) and acetyl salicylic acid, as defined in claim 2, and a pharmaceutically acceptable diluent or carrier.

13. A pharmaceutical composition comprising a co-crystal of the compound of formula (I) and acetyl salicylic acid, as defined in claim 3, and a pharmaceutically acceptable diluent or carrier.

14. A pharmaceutical composition comprising a co-crystal of the compound of formula (I) and acetyl salicylic acid, as defined in claim 4, and a pharmaceutically acceptable diluent or carrier.

15. A method of treating arterial thrombotic complications in patients with coronary artery, cerebrovascular or peripheral vascular disease by administering a therapeutically effective amount of a co-crystal of the compound of formula (I) and acetyl salicylic acid as defined in claim 2.

16. A method of treating arterial thrombotic complications in patients with coronary artery, cerebrovascular or peripheral vascular disease by administering a therapeutically effective amount of a co-crystal of the compound of formula (I) and acetyl salicylic acid as defined in claim 3.

17. A method of treating arterial thrombotic complications in patients with coronary artery, cerebrovascular or peripheral vascular disease by administering a therapeutically effective amount of a co-crystal of the compound of formula (I) and acetyl salicylic acid as defined in claim 4.

* * * * *